United States Patent [19]

Blank et al.

[11] 4,349,471

[45] Sep. 14, 1982

[54] PROCESS FOR THE PREPARATION OF AROMATIC SULPHONIC ACID HALIDES

[75] Inventors: Heinz U. Blank, Odenthal; Erich Wolters, Niederzier; Norbert Langenfeld, Cologne, all of Fed. Rep. of Germany

[73] Assignee: Bayer Aktiengesellschaft, Leverkusen, Fed. Rep. of Germany

[21] Appl. No.: 227,445

[22] Filed: Jan. 22, 1981

[30] Foreign Application Priority Data

Feb. 8, 1980 [DE] Fed. Rep. of Germany ....... 3004693

[51] Int. Cl.[3] ................. C07C 107/04; C07C 143/70; C07C 107/06; C07C 51/58; C07C 63/04; C07C 63/10; C07C 65/01; C07C 51/16; C07C 51/255; C07C 147/107
[52] U.S. Cl. ..................................... 260/208; 260/196; 260/200; 260/201; 260/205; 260/206; 260/207; 260/207.1; 260/453 AP; 260/453 AR; 260/543 R; 260/544 D; 260/544 B; 260/544 S; 260/544 N; 260/544 P; 260/544 L; 560/12; 560/13; 560/14; 560/25; 560/27; 560/28; 560/138; 560/139; 560/142; 562/427; 562/428; 562/429; 562/430; 260/192
[58] Field of Search ........... 260/543 R, 544 D, 544 B, 260/544 S, 544 N, 544 P, 544 L, 197, 194, 200, 196, 201, 207.1, 205, 208, 206, 192, 207; 562/408, 422, 427, 428, 429, 430; 560/12, 13, 14, 142, 138, 139

[56] References Cited

U.S. PATENT DOCUMENTS 3,686,301  8/1972  Kirch .............................. 260/543 R

FOREIGN PATENT DOCUMENTS 574836  4/1933  Fed. Rep. of Germany .

Primary Examiner—Natalie Trousof
Assistant Examiner—Frederick W. Pepper
Attorney, Agent, or Firm—Sprung, Horn, Kramer & Woods

[57] ABSTRACT

A process for the simultaneous preparation of an aromatic sulphonic acid halide and an aromatic carboxylic acid halide or the corresponding carboxylic acid is disclosed wherein an aromatic sulphonic acid or acid anhydride is reacted with an aromatic trihalogenomethyl compound in the presence of a Brönsted acid or Lewis acid at a temperature of 20° to 300° C., if appropriate in the presence of a solvent. Generally, at least half an equivalent of aromatic trihalogenomethyl compound is employed per equivalent of sulphonic acid.

19 Claims, No Drawings

PROCESS FOR THE PREPARATION OF AROMATIC SULPHONIC ACID HALIDES

The invention relates to a process for the simultaneous preparation of aromatic sulphonic acid halides and aromatic carboxylic acid halides or the corresponding carboxylic acids by reaction of aromatic sulphonic acids with aromatic trihalogenomethyl compounds in the presence of a Brönsted acid or Lewis acid.

It is known from U.S. Pat. No. 3,686,301 that 3,5-dichlorosulpho-benzoyl chloride is obtained by reacting 3,5-disulpho-benzoic acid, heated to 180° C. with three times the molar amount of benzotrichloride, the benzotrichloride being added over a period of 3 hours, the temperature being slowly reduced to 130° C. during this addition and the mixture being stirred for a further hour at 130° C.

It is also known, from German Reichspatent No. 574,836, that the sodium salts of aromatic sulphonic acids can be reacted with benzotrichloride to give the corresponding aromatic sulphonic acid chloride. It is also indicated in this German Reichspatent that the known reaction of free carboxylic acids with benzotrichloride in the presence of zinc chloride for the preparation of carboxylic acid chlorides cannot be applied to free organic sulphonic acids.

A process has now been found for the simultaneous preparation of aromatic sulphonic acid halides and aromatic carboxylic acid halides or of the corresponding carboxylic acids by reaction of an aromatic sulphonic acid or sulphonic acid anhydride with an aromatic trihalogenomethyl compound, which is characterised in that at least half an equivalent of an aromatic trihalogenomethyl compound is reacted per equivalent of sulphonic acid, in the presence of a Brönsted acid or Lewis acid at a temperature of 20°–300° C., if appropriate in an inert solvent.

Examples of aromatic sulphonic acids which can be employed in the process according to the invention are those of the general formula

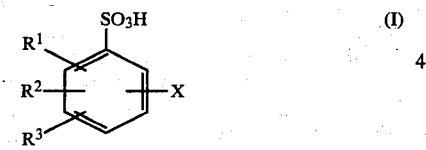

in which
X represents hydrogen,

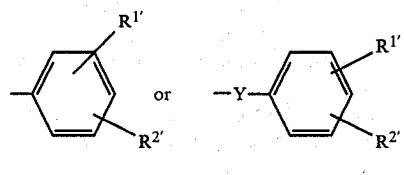

wherein
Y represents —O—, —SO$_2$—, —N=N— or —CH$_2$ and R$^1$, R$^2$, R$^3$, R$^{1'}$ and R$^{2'}$ independently of one another denote hydrogen, alkyl, cycloalkyl, aryl, aralkyl, hydroxyl, alkoxy, acyloxy, halogen, acylamino, N-carbalkoxyamino,
N-carbaryloxyamino, nitro, the sulphonic acid group, the carboxylic acid group, the carboxylic acid ester group or the urea group, and, furthermore, two of the radicals R$^1$, R$^2$ and R$^3$ which are adjacent can be part of a fused-on cycloaliphatic or aromatic ring which is optionally substituted by a sulphonic acid group.

Instead of the sulphonic acids mentioned, it is also possible to employ the corresponding sulphonic acid anhydrides.

Examples of aromatic trihalogenomethyl compounds which can be employed for the process according to the invention are those of the general formula

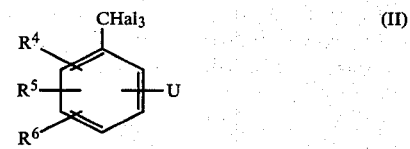

in which
U represents hydrogen,

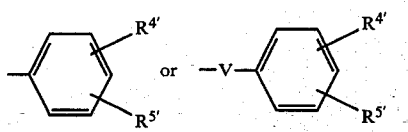

wherein
V represents —O—, —SO$_2$—, —N=N— or —CH$_2$—,
R$^4$, R$^5$, R$^6$, R$^{4'}$ and R$^{5'}$ independently of one another denote hydrogen, alkyl, cycloalkyl, aryl, aralkyl, alkoxy, aryloxy, CHal$_3$, halogen, isocyanato, N-carbalkoxyamino or N-carbaryloxyamino and, furthermore,
two of the radicals R$^4$, R$^5$ and R$^6$ which are adjacent can be part of a fused-on cycloaliphatic or aromatic ring which is optionally substituted by CHal$_3$, and
Hal represents chlorine or bromine.

Examples of alkyl which may be mentioned are straight-chain or branched hydrocarbon radicals with 1 to 6, preferably 1 to 4 and particularly preferably 1 to 2, carbon atoms, such as methyl, ethyl, propyl, isopropyl, butyl, isobutyl, pentyl and hexyl.

Examples of cycloalkyl which may be mentioned are cyclopentyl and cyclohexyl, preferably cyclohexyl.

Examples of aryl which may be mentioned are aromatic carbocyclic radicals such as phenyl, naphthyl and anthryl, preferably phenyl, i.e. compounds having 6 to 18 carboxylic carbon atoms.

Examples of aralkyl which may be mentioned are hydrocarbon radicals with 1 to 6 carbon atoms in the aliphatic part and 6 to 14 carbon atoms in the aromatic part, such as benzyl, β-phenyl-ethyl, naphthylmethyl, naphthylethyl, anthrylmethyl, γ-phenyl-propyl and β-phenyl-n-hexyl. Benzyl is the preferred aralkyl.

Examples of alkoxy which may be mentioned are straight-chain or branched radicals of aliphatic alcohols with 1 to 6, preferably 1 to 4 and in particular 1 to 2, carbon atoms, such as methoxy, ethoxy, propoxy, isopropoxy, butoxy, isobutoxy, pentyloxy and hexyloxy.

Aryloxy which may be mentioned are radicals of aromatic hydroxy compounds with 6 to 14 carbon atoms, such as phenoxy, naphthyloxy and anthryloxy, preferably phenoxy.

Examples of halogen which may be mentioned are fluorine, chlorine, bromine and iodine, preferably fluorine, chloride and bromine and particularly preferably chlorine and bromine.

In the case where two of the radicals $R^1$ to $R^3$ or $R^4$ to $R^6$ which are adjacent can be parts of a fused-on cycloaliphatic or aromatic ring, there may be understood, with the inclusion of the benzene nucleus of the formula (I) or of the formula (II), the indane, indene, tetrahydronaphthalene and naphthalene system. The preferred fused ring systems are the naphthalene system and the tetrahydronaphthalene system. The naphthalene system is particularly preferred.

Examples which may be mentioned of preferred aromatic sulphonic acid for the process according to the invention are those of the formula

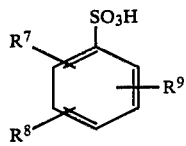

in which
$R^7$, $R^8$ and $R^9$ independently of one another denote hydrogen, $C_1$-$C_4$-alkyl, phenyl, benzyl, methoxy, ethoxy, phenoxy, fluorine, chlorine, bromine, nitro or the sulphonic acid group,
and in which, furthermore,
two of the radicals $R^7$ to $R^9$ which are adjacent can be part of a fused-on cycloaliphatic or aromatic 6-membered ring.

Aromatic sulphonic acids which may be mentioned as particularly preferred for the process according to the invention are those of the general formula

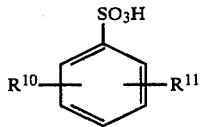

in which
$R^{10}$ and $R^{11}$ independently of one another denote hydrogen, methyl ethyl, chlorine or fluorine,
and in which
$R^{10}$ and $R^{11}$, if they are adjacent, can be part of a fused-on cycloaliphatic or aromatic 6-membered ring. When $R^{10}$ or $R^{11}$ are part of a cycloaliphatic ring, it preferably has 4 to 12 carbocyclic carbon atoms. Cycloalkane rings are particularly contemplated.

Examples which may be mentioned of aromatic sulphonic acids for the process according to the invention are: benzenesulphonic acid, 2-, 3- and 4-toluenesulphonic acid, 2-, 3- and 4-chloro-benzenesulphonic acid, 2,5- and 3,4-dichloro-benzenesulphonic acid, benzene-1,3-disulphonic acid, 2-chloro-toluene-4-sulphonic acid, 4-chloro-toluene-2-sulphonic acid, toluene-2,4-disulphonic acid, 1-acetylamino-benzene-4-sulphonic acid, 4-carbomethoxyamino-benzenesulphonic acid, 1- and 2-naphthalene-sulphonic acid, naphthalene-1,5-, 2,6- and 2,7-disulphonic acid, 4-biphenylsulphonic acid, 4,4'-biphenyl-disulphonic acid, 4-phenoxy-benzenesulphonic acid and diphenylmethane-4-sulphonic acid.

Aromatic trichloromethyl compounds may be mentioned in particular as aromatic trihalogenomethyl compounds for the process according to the invention. Examples of trichloromethyl compounds are those of the general formula

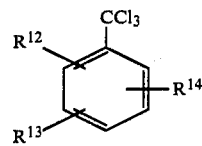

in which
$R^{12}$, $R^{13}$ and $R^{14}$ independently of one another denote hydrogen, chlorine, trifluoromethyl or trichloromethyl,
and in which
two of the radicals $R^{12}$ to $R^{14}$ which are adjacent can be parts of a fused-on cycloaliphatic or aromatic 6-membered ring.

Trichloromethyl compounds of the general formula (VI)

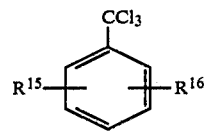

in which
$R^{15}$ and $R^{16}$ independently of one another denote hydrogen, methyl, chlorine or trichloromethyl,
and in which
the radicals $R^{15}$ and $R^{16}$, if they are adjacent, can be parts of a fused-on cycloaliphatic or aromatic 6-membered ring.
are particularly preferably employed in the process according to the invention.

The following trichloromethyl compounds may be mentioned as examples, benzotrichloride, 1-chloro-2-trichloromethylbenzene, 1-chloro-4-trichloromethyl-benzene, 2,4-dichloro-1-trichloromethylbenzene, 1,3-bis-(trichloromethyl)-benzene, 1,4-bis-(trichloromethyl)-benzene, 1-trichloromethyl-naphthalene, 2-trichloromethylnaphthalene, 4-trichloromethyl-biphenyl, 4,4'-bis-(trichloromethyl)-biphenyl, 4-trichloromethyl-diphenyl ether, 4-trichloromethyl-diphenyl-methane, benzotribromide, 1-bromo-2-tribromomethylbenzene and 1-bromo-4-tribromomethylbenzene.

In the process according to the invention, the reaction of aromatic sulphonic acids of the formula (III) with aromatic trichloromethyl compounds of the formula (V) is preferred, and the reaction of sulphonic acids of the formula (IV) with trichloromethyl compounds of the formula (VI) is particularly preferred.

The process according to the invention is carried out in the presence of a Brönsted acid or Lewis acid. A Brönsted acid is in general characterised in that it contains a dissociable hydrogen atom; a Lewis acid is in general characterised in that it has a gap for an electron pair (in this context, see text book of theoretical chemistry, for example H. A. Staab, Einführung in die theoretische organische Chemie (Introduction to Theoretical Organic Chemistry), 3rd Edition, page 599 et seq., Verlag Chemie, Weinheim 1962). Examples of Brönsted acids for the process according to the invention are sulphuric acid, pyrosulphuric acid, phosphoric acid, pyrophosphoric acid and the acid salts of these acids, and furthermore polyphosphoric acid, fluorosulphonic acid, chlorosulphonic acid and bromosulphonic acid. Examples of Lewis acids for the process according to the invention are aluminum chloride, iron chloride, zinc chloride, cadmium chloride, mercury-II chloride, beryllium chloride, magnesium chloride, boron trifluoride, boron trichloride, gallium chloride, titanium dichloride, titanium tetrachloride, zirconium tetrachloride, nickel chloride, niobium pentachloride, uranium tetrachloride, copper-I chloride, copper-II chloride, cobalt chloride, chromium trichloride, bisumth trichloride, antimony trichloride, antimony pentachloride, tellurium tetrachloride, arsenic trichloride and arsenic pentachloride. The Brönsted acids and Lewis acids mentioned can be employed both individually and as a mixture of different Brönsted acids, as a mixture of different Lewis acids and as a mixture of Brönsted acids and Lewis acids.

The process according to the invention is preferably carried out in the presence of sulphuric acid, chlorosulphonic acid, iron-III chloride, zinc chloride or a mixture of these substances. It is particularly preferably carried out in the presence of sulphuric acid or iron-III chloride. It can also be sufficient, for the process according to the invention, for sulphonating agents such as those which technical grade sulphonic acids contain from the preparation process, for example sulphuric acid or chlorosulphonic acid, to be present.

The Brönsted acid or Lewis acid is employed in the process according to the invention in an amount of, for example, 0.01 to 20 mol %, preferably of 0.1 to 10 mol %, relative to the sulphonic acid employed.

The process according to the invention can be carried out at 20°–300° C., for example at a temperature of 30° to 130° C., preferably 40° to 110° and particularly preferably 50° to 95° C.

The pressure is not critical for the ease with which the process according to the invention is carried out, so that the process can be carried out under normal pressure, increased pressure or reduced pressure. The preferred variant is that under normal pressure.

The process according to the invention can be carried out with or without an additional reaction medium. Suitable reaction media are those which are inert under the reaction conditions, for example halogenated hydrocarbons, such as chloroform, carbon tetrachloride, trichloroethane, tetrachloroethane, pentachloroethane, chlorobenzene, dichlorobenzene, chlorotoluene or dichlorotoluene. Trihalogenomethyl compound employed in excess or the aromatic carboxylic acid chloride formed in the course of the reaction can also serve as the reaction medium. The preferred variant is that without an additional solvent.

For complete conversion of the aromatic sulphonic acid in the process according to the invention, it is necessary to employ at least half an equivalent of the aromatic trihalogenomethyl compound per equivalent of sulphonic acid. The corresponding benzoic acid is thereby formed from the aromatic trihalogenomethyl compound. In a preferred procedure, however, it is also possible to employ the aromatic trihalogenomethyl compound in an amount greater than half the equivalent amount, relative to the aromatic sulphonic acid, for example in an equimolar amount. In this case, the corresponding benzoyl halide is formed from the aromatic trihalogenomethyl compound. It is furthermore possible to employ the aromatic trihalogenomethyl compound in excess, relative to the aromatic sulphonic acid, for example in an amount of up to 5 equivalents per equivalent of sulphonic acid. In this latter variant, the excess aromatic trihalogenomethyl compound serves as a solvent or diluent. An even greater excess is not critical for the process according to the invention, but is less favourable for economic reasons.

The reaction of the process according to the invention may be represented by the following equations using the reaction of benzenesulphonic acid with benzotrichloride at various ratios of equivalents of aromatic sulphonic acid and aromatic trihalogenomethyl compound as an example:

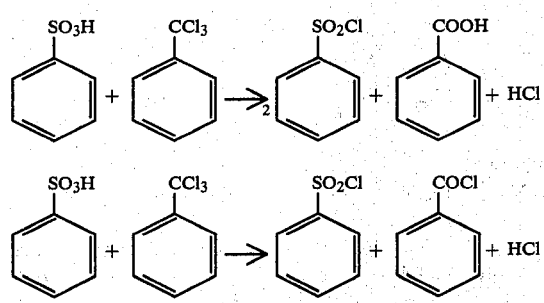

Aromatic sulphonic acid halides of the general formula

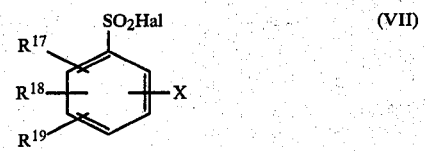

in which

X represents hydrogen,

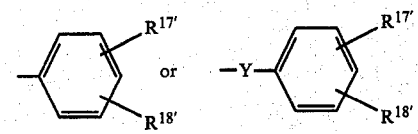

wherein

Y represents —O—, —SO$_2$—, —N=N— or —CH$_2$—,

R$^{17}$, R$^{18}$, R$^{19}$, R$^{17'}$ and R$^{18'}$ have the meanings of R$^1$, R$^2$, R$^3$, R$^{1'}$ and R$^{2'}$, but the halogenosulphonyl group —SO$_2$Hal replaces the sulphonic acid group —SO$_3$H and the carboxylic acid halide group —COHal replaces the carboxylic acid group —CO$_2$H, and Hal represents chlorine or bromine, can accordingly be prepared in the process according to the invention.

The following sulphonyl chlorides are preferably prepared in the process according to the invention: benzenesulphonyl chloride, 2-, 3- and 4-toluenesulphonyl chloride, 2-, 3- and 4-chlorobenzenesulphonyl chloride, benzene-1,3-disulphonyl chloride and 1- and 2-naphthalenesulphonyl chloride.

In the process according to the invention, the aromatic trihalogenomethyl compound employed is converted into the corresponding aromatic carboxylic acid compound of the general formula

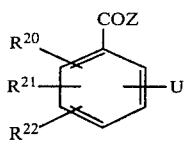

in which

U represents hydrogen,

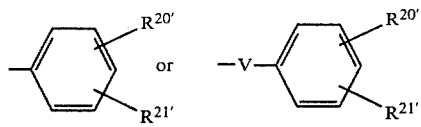

wherein

V represents —O—, —SO$_2$—, —N═N— or —CH$_2$—,

R$^{20}$, R$^{21}$, R$^{22}$, R$^{20'}$ and R$^{21'}$ have the scope of meaning of R$^4$, R$^5$, R$^6$, R$^{4'}$ and R$^{5'}$, but the group —COZ appears instead of the trihalogenomethyl group —CHal$_3$, and Z represents hydroxyl, chlorine or bromine.

In addition to the preparation of the aromatic sulphonic acid halide, the process according to the invention thus simultaneously permits the preparation of an aromatic carboxylic acid or, preferably, its corresponding carboxylic acid halide. As a result, there is not only a possibility of wide variation with regard to the preparation of the aromatic sulphonic acid halide, but also, by choosing the aromatic trihalogenomethyl compound within the scope of the formula (II) and by choosing in the manner described the ratio of the number of equivalents of aromatic sulphonic acid to aromatic trihalogenomethyl compound, there is the possibility of wide variation with regard to the simultaneous preparation either of an aromatic carboxylic acid or its corresponding carboxylic acid halide, and the substitution of this aromatic carboxylic acid or of its carboxylic acid halide.

In the process according to the invention, the starting substances can be added in any desired sequence. Thus, for example, it is possible to bring together the aromatic sulphonic acid, the aromatic trihalogenomethyl compound and the Brönsted acid or Lewis acid successively. However, it is also possible to initially introduce the Brönsted acid or Lewis acid into the reaction vessel and then to add the aromatic sulphonic acid and the aromatic trihalogenomethyl compound successively or simultaneously, in the latter case separately or as a mixture.

The process according to the invention can be carried out batchwise or continuously. The continuous process can be carried out, for example, in a circulatory reactor known to the expert. In this procedure, the starting substances are added at one point of the circulatory reactor, via one or more inlets, whilst at the least some of the reaction mixture is removed again from the reactor, after flowing through the circulatory reactor, at a point shortly before reaching the points of addition again. The reaction mixture removed is worked up by customary methods, for example by fractional distillation. At least some of the residue thereby obtained, which can contain the Brönsted acid or Lewis acid, can be recycled to the circulatory reactor.

In the batchwise procedure, for example, the Brönsted acid or Lewis acid is added to the aromatic sulphonic acid and the aromatic trihalogenomethyl compound in a stirred apparatus and the mixture is heated to the reaction temperature, whilst stirring, until the evolution of gas has ended. Working up is carried out by known methods, for example by fractional distillation, but also by extraction or other processes.

The gaseous hydrogen chloride obtained in the reaction can be collected in a suitable absorption apparatus, for example as aqueous or alcoholic hydrochloric acid. However, it can also be compressed in a pure form and put to further use in this form.

The aromatic sulphonic acid chlorides which can be prepared according to the invention and the aromatic carboxylic acids simultaneously formed, or the corresponding aromatic carboxylic acid halides, are known to the expert as indispensable intermediate products for a large number of syntheses, for example for esters, amides, hydrazides and other derivatives of sulphonic acids or carboxylic acids for dyestuffs, medicaments and other products.

Compared with the preparation of the sulphonic acid chlorides by chlorosulphonation, the process according to the invention provides the advantage that no waste acids are formed. Compared with the process using thionyl chloride or phosgene with dialkylformamide catalyst, it provides the advantage that no off-gas mixtures which are difficult to separate are obtained and that no potentially carcinogenic dialkylcarbamic acid chlorides can be formed. Compared with the uncatalysed reaction of aromatic sulphonic acids with trichloromethyl-aromatic compounds, the process according to the invention has the advantage of considerably reduced reaction temperatures and times. A further advantage is that the aromatic trihalogenomethyl compound to be used can be varied greatly according to its availability, the ease of separation of the product mixture and the demand for the aromatic carboxylic acid simultaneously formed or for the corresponding aromatic sulphonic acid halide. If appropriate, the amount of aromatic trihalogenomethyl compound employed can be greatly reduced in comparison with the process of the state of the art.

EXAMPLE 1 (COMPARISON EXAMPLE) AND 2

In each case 158 g (1 mol) of benzenesulphonic acid (98.5% pure, free from sulphuric acid) and 195.5 g (116 ml, 1 mol) of benzotrichloride (98.5% pure) are heated to 60° C. in a glass flask with a stirrer, an internal thermometer and a reflux consenser with a bubble counter. After about ½ an hour and when the evolution of gas has subsided, the first sample is taken (0 hour sample). In Example 1, heating is then continued and a sample is taken after each of the times indicated.

In Example 2, after the 0 hour sample, 7.9 g (8 mol %) of sulphuric acid are added and samples are taken, in each case after the same intervals of time, and are investigated by gas chromatography. Table 1 shows the yields after the appropriate reaction times. In this table, PhSO$_2$Cl denotes benzenesulphonic acid chloride, PhCOCl denotes benzoyl chloride and PhCCl$_3$ denotes benzotrichloride. Percentage data in all the examples are relative to the theoretical yield.

TABLE 1

| Reaction time after the evolution of gas has ended | Example 1 | | | Example 2 | | |
|---|---|---|---|---|---|---|
| | PhSO$_2$Cl % | PhCOCl % | PhCCl$_3$ % | PhSO$_2$Cl % | PhCOCl % | PhCCl$_3$ % |
| 0 hour | 8 | 56 | 44 | 5 | 52 | 43 |
| 0.5 hour | 9 | 58 | 42 | 89 | 85 | 3 |
| 2 hours | 14 | 60 | 40 | 90 | 87 | 0 |
| 24 hours | 64 | 88 | 12 | | | |
| 48 hours | 81 | 94 | 6 | | | |
| 120 hours | 84 | 96 | 4 | | | |

EXAMPLES 3 AND 4 (COMPARISON EXAMPLES)

158 g (1 mol) of benzenesulphonic acid (98.5% pure, free from sulphuric acid) are initially introduced into a glass flask with a stirrer, internal thermometer, dropping funnel and reflux condenser and are warmed to 60° or 110° C. (see Table 2). 195.5 g (116 ml, 1 mol) of benzotrichloride are added dropwise in the course of three hours. The mixture is then subsequently stirred at the above temperature for 1 hour. The product mixture is subjected to fractional distillation over a mirrored column (3 cm×30 cm) under 10 mbar.

The yields are given in Table 2.

TABLE 2

| Example | 3 | 4 |
|---|---|---|
| Reaction temperature | 60° | 110° |
| Ph-SO$_2$Cl (%) | 21 | 72 |
| Ph-COCl (%) | 67 | 86 |

EXAMPLES 5 TO 8

Examples 5 to 8 were carried out analogously to Example 3, in the same bath size, but in each case a defined amount of catalyst is added to the benzenesulphonic acid. The data can be found in Table 3 below.

TABLE 3

| Example | Catalyst | Amount | Temperature | PhSO$_2$Cl | PhCOCl |
|---|---|---|---|---|---|
| 5 | FeCl$_3$ | 1.0 g | 60° | 93% | 98% |
| 6 | H$_2$SO$_4$ | 7.9 g | 60° | 84% | 96% |
| 7 | H$_2$SO$_4$ | 7.9 g | 110° | 87% | 96% |
| 8 | H$_2$SO$_4$ | 4.0 g | 60° | 85% | 96% |

EXAMPLE 9

2,500 g (14.8 mols) of a 93.8% pure benzenesulphonic acid which has been prepared by sulphonation of benzene with SO$_3$ and contains 1.8% by weight of H$_2$SO$_4$ is reacted with 3,093 g (15.6 mols) of benzotrichloride (98.5% pure) at 110° C. analogously to Example 4.

Distillation is carried out under 10 mbars over a 1 m mirrored column ($\phi$ 5 cm, packing: 5×5 mm Raschig rings).

| Fraction | Amount (g) | Benzoyl chloride | Content (%) Benzotrichloride | Benzenesulphonyl chloride |
|---|---|---|---|---|
| 1 | 1,954.3 | 99.5 | — | — |
| 2 | 275.9 | 38.6 | 5.7 | 52.3 |
| 3 | 2,114.5 | — | — | 99.5 |

Yield: benzoyl chloride: 93.6%; benzenesulphonyl chloride: 85.9%.

EXAMPLE 10

158 g (1 mol) of benzenesulphonic acid (98.5% pure) and 1.0 g of FeCl$_3$ are reacted with 97.8 g (0.5 mol) of benzotrichloride (98.5% pure) at 95° C. analogously to Example 3.

Yield: benzenesulphonyl chloride: 80%; benzoic acid: 76%.

EXAMPLE 11

172 g (1 mol) of p-toluenesulphonic acid (90% pure) and 4 g of sulphuric acid are reacted with 207 g (1.06 mol) of benzotrichloride at 80° C. analogously to Example 3.

Yield: p-toluenesulphonyl chloride: 93.6%; benzoyl chloride: 97.1%; benzotrichloride: 2.2%.

EXAMPLE 12

158 g (1 mol) of benzenesulphonic acid (98.5% pure) and 4 g of sulphuric acid are reacted with 166 g (0.53 mol) of 1,3-bis-(trichloromethyl)-benzene analogously to Example 4.

Yield: benzenesulphonyl chloride: 94.3%; isophthaloyl chloride: 92.1%; 1,3-bis-(trichloromethyl)-benzene: 2.8%.

EXAMPLE 13

977.5 g (5 mols) of benzotrichloride (98.5% pure) are added, in the course of one hour at 95° C., to 841.5 g (5 mols) of a 94% pure benzenesulphonic acid which has been prepared by sulphonation of benzene with SO$_3$ and contains 1.8% of H$_2$SO$_4$. The mixture is then subsequently stirred at 95° C. for one hour. Distillation is carried out under 10 mbar over a mirrored column (3 cm×30 cm).

Yield: benzoyl chloride: 96.3%; benzenesulphonyl chloride: 87.8%.

What is claimed is:

1. A process for the simultaneous preparation of an aromatic sulphonic acid halide and an aromatic carboxylic acid halide or the corresponding carboxylic acid which comprises contacting an aromatic sulphonic acid or an aromatic sulphonic acid anhydride with an aromatic trihalogenomethyl compound in the presence of at least 0.01 mol percent, relative to the aromatic sulphonic acid, of a Brönsted acid or Lewis acid at a temperature of 20° to 300° C., the reaction mixture containing at least half an equivalent of said aromatic trihalogenomethyl compound per equivalent of sulphonic acid.

2. A process according to claim 1, wherein the process is carried out in the presence of an inert solvent.

3. A process according to claim 1, wherein the trihalogenomethyl compound is a trichloromethyl compound.

4. A process according to claim 1, wherein the Brönsted acid or Lewis acid is sulfuric acid, chlorosulfuric acid, iron-III chloride or zinc chloride.

5. A process according to claim 1, wherein the process is carried out in the presence of 0.01 to 20 mol percent, relative to the aromatic sulphonic acid, of a Brönsted acid or Lewis acid.

6. A process according to claim 1, wherein the process is carried out at 30° to 130° C.

7. A process according to claim 1, wherein at least an equivalent of the aromatic trihalogenomethyl compound, relative to the aromatic sulphonic acid is employed for the preparation of the aromatic sulphonic halide in the simultaneous preparation of the aromatic carboxylic acid halide corresponding to the aromatic trihalogenomethyl.

8. A process according to claim 1, wherein half the equivalent amount of the aromatic trihalogenomethyl compound, relative to the aromatic sulphonic acid, is employed for the preparation of the aromatic sulphonic acid halide and for the simultaneous preparation of the aromatic carboxylic acid corresponding to the aromatic trihalogenomethyl compound.

9. A process according to claim 1, wherein the aromatic sulphonic acid has the formula

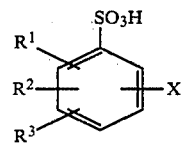

in which
X represents hydrogen,

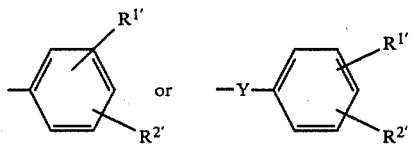

wherein
Y represent —O—, —SO$_2$—; —N=N— or —CH$_2$— and R$^1$, R$^2$, R$^3$, R$^{1'}$ and R$^{2'}$ independently of one another denote hyrogen, alkyl, cycloalkyl, aryl, aralkyl, hydroxy, alkoxy, acyloxy, halogen, acylamino, N-carbalkoxyamino, N-carbaryloxyamino, nitro, the sulphonic acid group, the carboxylic acid group the carboxylic acid ester group or the urea group and furthermore
two of the radicals R$^1$ and R$^2$ and R$^3$ which are adjacent can be part of a fused-on cycloaliphatic or aromatic ring which is optionally substituted by a sulphonic acid group.

10. A process according to claim 1, wherein anhydride of an aromatic sulphonic acid is employed and the anhydride is an anhydride of an aromatic sulphonic acid of the formula

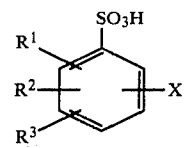

in which
X represents hydrogen,

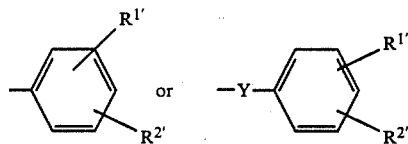

wherein
Y represents —O—, —SO$_2$—; —N=N— or —CH$_2$— and R$^1$, R$^2$, R$^3$, R$^{1'}$ and R$^{2'}$ independently of one another denote hydrogen, alkyl, cycloalkyl, aryl, aralkyl, hydroxyl, alkoxy, acyloxy, halogen, acylamino, N-carbalkoxyamino, N-carbaryloxyamino, nitro, the sulphonic acid group, the carboxylic group, the carboxylic acid ester group or the urea group, and furthermore
two of the radicals R$^1$, R$^2$ and R$^3$ which are adjacent can be part of a fused-on cycloaliphatic or aromatic ring which is optionally substituted by a sulphonic acid group.

11. A process according to claim 1, wherein said aromatic trihalogenomethyl compound has the formula

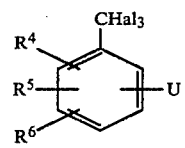

in which
U represents hydrogen,

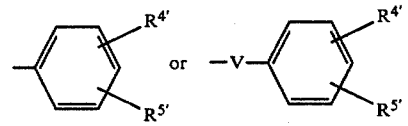

wherein
V represents —O—, —SO$_2$—, —N=N— or —CH$_2$—, R$^4$, R$^5$, R$^6$, R$^{4'}$ and R$^{5'}$ independently of one another denote hydrogen, alkyl, cycloalkyl, aryl, aralkyl alkoxy, aryoxy, CHal$_3$, haogen, isocyanato, N-carbalkoxyamino or N-carbaryloxyamino and furthermore,
two of the radicals R$^4$, R$^5$ and R$^6$ which are adjacent can be part of a fused-on cycloaliphatic or aromatic ring which is optionally substituted by CHal$_3$, and
Hal represents chlorine or bromine.

12. A process according to claim 1, wherein the aromatic sulphonic acid or aromatic sulphonic acid anhydride is an acid or anhydride, the free acid form of which has the following formula

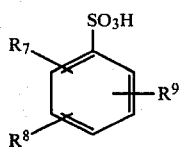

in which
R⁷, R⁸ and R⁹ independently of one another denote hydrogen, C₁–C₄-alkyl, phenyl, benzyl, methoxy, ethoxy, phenoxy, fluorine, chlorine, bromine, nitro or the sulphonic acid group,
and in which, furthermore
two of the radicals R⁷ to R⁹ which are adjacent can be part of a fused-on cycloaliphatic or aromatic 6-membered ring.

13. A process according to claim 1 wherein aromatic sulphonic acid or aromatic sulphonic acid anhydride has in the free acid form the formula

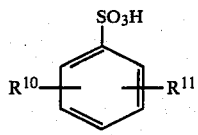

in which
R¹⁰ and R¹¹ independently of one another denote hydrogen, methyl, ethyl, chlorine or fluorine,
and in which
R¹⁰ and R¹¹, if they are adjacent, can be part of a fused-on cycloaliphatic or aromatic 6-membered ring.

14. A process according to claim 1, wherein the aromatic trihalogenomethyl compound has the formula

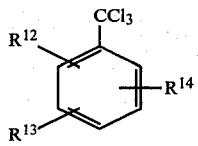

in which
R¹², R¹³ and R¹⁴ independently of one another denote hydrogen, chlorine, trifluoromethyl or trichloromethyl,
and in which
two of the radicals R¹² to R¹⁴ which are adjacent can be parts of a fused-on cycloaliphatic or aromatic 6-membered ring.

15. A process according to claim 1, wherein said aromatic trihalogenomethyl compound has the formula

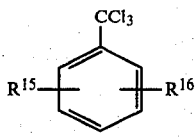

in which
R¹⁵ and R¹⁶ independently of one another denote hydrogen, methyl, chlorine or trichloromethyl,
and in which
the radicals R¹⁵ and R¹⁶ if they are adjacent can be parts of a fused-on cycloaliphatic or aromatic 6-membered ring.

16. A process according to claim 1, wherein said Brönsted acid or Lewis acid is aluminum chloride, iron chloride, zinc chloride, cadmium chloride, mercury-II chloride, beryllium chloride, magnesium chloride, boron trifluoride, boron trichloride, gallium chloride, titanium dichloride, titanium tetrachloride, zirconium tetrachloride, nickel chloride, niobium pentachloride, uranium tetrachloride, copper-i chloride, copper-II chloride, cobalt chloride, chromium trichloride, bismuth trichloride, antimony trichloride, antimony pentachloride, tellurium tetrachloride, arsenic trichloride or arsenic pentachloride.

17. A process according to claim 1, wherein said aromatic sulphonic acid or aromatic sulphonic acid anhydride has in its free acid form the formula

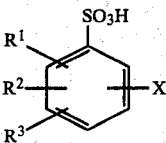

in which
X represents hydrogen,

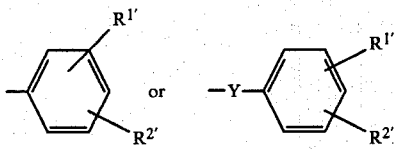

wherein
Y represent —O—, —SO₂—; —N=N— or —CH₂
and
R¹, R², R³, R¹' and R²' independently of one another denote hydrogen, alkyl, cycloalkyl, aryl, aralkyl, hydroxy, alkoxy, acyloxy, halogen, acylamino, n-carbalkoxyamino, N-carbaryloxyamino, nitro, the sulphonic acid group, the carboxylic acid ester group or the urea group and furthermore
two of the radicals R¹ and R² and R³ which are adjacent can be part of a fused-on cycloaliphatic or aromatic ring which is optionally substituted by a sulphonic acid group.

18. A process according to claim 1, wherein the process is carried out in the presence of a Brönsted acid.

19. A process according to claim 18, wherein said Brönsted acid is sulphuric acid, pyrosulphuric acid, phosphoric acid, pyrophosphoric acid, a salt of one of such acids, polyphosphoric acid, fluorosulphonic acid, chlorosulphonic acid, bromosulphonic acid or a mixture thereof.

* * * * *